United States Patent [19]

Isogai et al.

[11] Patent Number: 4,678,858
[45] Date of Patent: Jul. 7, 1987

[54] PROCESS FOR PRODUCING ETHANOL

[75] Inventors: Nobuo Isogai; Takashi Okawa; Motoyuki Hosokawa; Tomoji Tsuji; Natsuko Wakui, all of Niigata, Japan

[73] Assignee: Agency of Industrial Science and Technology, Tokyo, Japan

[21] Appl. No.: 844,008

[22] Filed: Mar. 26, 1986

[30] Foreign Application Priority Data

Jun. 10, 1985 [JP] Japan .................. 60-124268

[51] Int. Cl.$^4$ ............... C07C 29/00; C07C 31/08
[52] U.S. Cl. ................... 568/902; 560/265; 568/487; 568/672
[58] Field of Search ................... 568/902 H

[56] References Cited

U.S. PATENT DOCUMENTS

| | | | |
|---|---|---|---|
| 2,623,906 | 12/1952 | Gresham | 568/902 |
| 4,126,752 | 11/1978 | Norotny et al. | 568/902 |
| 4,133,966 | 1/1979 | Pretzer et al. | 568/902 |
| 4,205,190 | 5/1980 | Gane et al. | 568/902 |
| 4,423,257 | 12/1983 | Isogai et al. | 568/902 |
| 4,424,383 | 1/1984 | Cornils et al. | 568/902 |
| 4,451,678 | 5/1984 | Isogai et al. | 568/902 |

FOREIGN PATENT DOCUMENTS

| | | | |
|---|---|---|---|
| 114536 | 7/1982 | Japan | 568/902 |
| 65231 | 4/1983 | Japan | 568/902 |
| 219134 | 12/1983 | Japan | 568/902 |

OTHER PUBLICATIONS

Wender et al., "Science" vol. 113, 1951, pp. 206, 207.

*Primary Examiner*—J. E. Evans
*Attorney, Agent, or Firm*—Browdy and Neimark

[57] ABSTRACT

A process for producing ethanol which comprises reacting methanol, carbon monoxide and water in the presence of a catalyst comprising cobalt or a cobalt compound and a tertiary phosphine as an effective component is disclosed. A gaseous mixture obtained by burning heavy oil or coal having a relatively high content of carbon can be used as a raw material for producing ethanol.

9 Claims, No Drawings

PROCESS FOR PRODUCING ETHANOL

BACKGROUND OF THE INVENTION

1. Object of the Invention

This invention relates to a process for producing ethanol from methanol, carbon monoxide and water.

2. Prior Art

It was known in prior art that ethanol could be produced by reacting methanol, carbon monoxide and hydrogen. A variety of catalysts therefor have been found. Mixed gas of carbon monoxide and hydrogen as a raw material is used in the prior process for producing ethanol. It is clear from the reaction equation that 2 mol of hydrogen is necessary per 1 mol of carbon monoxide. When the molar ratio of hydrogen to carbon monoxide becomes smaller, a large amount of such by-products as acetaldehyde, acetic acid and methyl acetate are formed, thereby reducing the selectivity to ethanol. So, when a gaseous mixture obtained by burning heavy oil or coal having a relatively high content of carbon is used as a carbon monoxide source, there is insufficient hydrogen. There are various problems connected with using hydrogen as a raw material. This means that the plant must be set up at locations where hydrogen is available at low cost.

SUMMARY OF THE INVENTION

An object of this invention is to provide a process for producing ethanol without hydrogen.

This invention relates to a process for producing ethanol which comprises reacting methanol, carbon monoxide and water in the presence of a catalyst comprising cobalt or a cobalt compound and a tertiary phosphine as an effective component.

DETAILED DESCRIPTION OF THE INVENTION

The amount of water employed may be in the range of 0.05–5 mol, and preferably 0.2–2 mol per 1 mol of methanol. When the amount of water employed is less than 0.05 mole per 1 mol of methanol, there is an increase in the amount of such byproducts as methyl acetate. When the amount of water employed is more than 5 mol per 1 mol of methanol, great energy is necessary for separating ethanol from the reaction solution due to increase in the amount of water in the solution.

The partial pressure of carbon monoxide may be more than 20 kg/cm$^2$G, and preferably in the range of 100–500 kg/cm$^2$G.

Although the use of hydrogen is unnecessary in the present invention, hydrogen may be present in the reaction system provided that the hydrogen partial pressure of less than 5 kg/cm$^3$G, preferably less than 1 kg/cm$^2$G. A hydrogen partial pressure of more than 5 kg/cm$^2$G lowers the reaction rate. Inert gas, such as nitrogen, argon, methane and the like may be present in the system.

The cobalt compounds employed in the practice of this invention include, for example, cobalt carbonyls, such as dicobalt octacarbonyl and cobalt hydride tetracarbonyl, an inorganic cobalt compound, such as cobalt hydroxide, cobalt carbonate or basic cobalt carbonate, an organic cobalt compound, such as a cobalt organic acids salt, cobaltocene or cobalt acetyl acetonate, or other cobalt compounds which produce cobalt carbonyl in the reaction system. The cobalt compound may be used alone or as a mixture. Dicobalt octacarbonyl is preferable.

The amount of the cobalt compound employed is in the range of 1–300 mg-atom, preferably 5–100 mg-atom in terms of cobalt per 1 mol of methanol. When the amount of cobalt compound is less than the lower limit mentioned above, though the reaction proceeds, the reaction rate is lowered. The use of cobalt compound in an amount of more than the upper limit merely adds to the production cost.

The tertiary phosphines of the present invention include, for example, triethyl phosphine, tri-n-propyl phosphine, tri-n-hexyl phosphine, tri-n-butyl phosphine, triphenyl phosphine, tri-p-tolylphosphine, tricyclohexyl phosphine, bis(1,4-diphenyl phosphino)butane and bis(1,6-diphenyl phosphino)hexane. Tri-n-butyl phosphine is preferable.

The amount of the tertiary phosphine may be employed so that the atomic ratio of cobalt to phosphorus is in the range of 1:0.2 to 1:8, preferably 1:0.5 to 1:5. The use of the tertiary phosphine in an amount of less than the lower limit will lessen the effectiveness in suppressing formation of esters or ethers. The use of tertiary phosphine in an amount of more than the upper limit lowers the reaction rate.

Use of solvent is not critical in this invention. However, it is preferable that the reaction is carried out in the presence of solvents which do not have a bad influence on the reaction.

Solvents which are inert to the reaction system include hydrocarbons and cyclic ethers. Hydrocarbon solvents include, for example, aromatic hydrocarbons, such as toluene, benzene and xylene; aliphatic hydrocarbons, such as hexane and octane; and alicyclic hydrocarbons, such as cyclohexane. The cyclic ethers include, for example 1,4-dioxane, tetrahydrofuran and the like.

The amount of the solvent employed may be in the range of 0–10 parts by weight, preferably 0.2–5 parts by weight per 1 part of methanol. Use of solvent in an amount of more than the above upper limit lowers the space/time yield of ethanol and is not practical.

The reaction temperature depends on the catalyst employed and other reaction conditions. In general, the temperature may be in the range of 180°–280° C., preferably 210°–250° C. Though the reaction proceeds at a temperature below 180° C., the reaction rate is low; at temperatures above 280° C. by-products form.

The present catalysts can be activated and used in the reaction in situ. But preferably, catalysts comprising a cobalt or cobalt compound and a phosphine may be activated by heat-treating at 180°–280° C. and under 50–500 kg/cm$^2$G in the presence of mixed gas of H$_2$ and CO (molar ratio of more than 0.25) and solvent. Methanol, carbon monoxide and water may be reacted in the presence of the activated catalyst.

The reaction mechanism of the present invention has not been theoretically clarified. However, since the reaction smoothly proceeds in the substantial absence of gaseous hydrogen, we assume that the hydride complex formed from water and cobalt carbonyl-phosphine complex plays an important part in the reaction.

Hydrogen and corrosive halogen, such as iodine or bromine are unnecessary according to the present invention. In addition, a high space time yield of ethanol and high selectivity to ethanol can be attained according to the present invention.

A synthesis gas containing hardly any hydrogen can be used in the present invention. In addition, lower grade methanol containing water anc also be used. The present invention is excellent from the industrial point of view.

The present process can be carried out batchwise or continuously.

The present invention is further illustrated by non-limiting Examples and Comparative runs.

In the following Examples and Comparative runs, the reactivity of methanol, selectivity to ethanol, substantial reactivity of methanol and selectivity to realizable ethanol are expressed by the following equations:

Reactivity of methanol (%) =

$$\frac{\text{mol of CH}_3\text{OH fed} - \text{mol of unreacted CH}_3\text{OH}}{\text{mol of CH}_3\text{OH fed}} \times 100$$

Selectivity to each product (%) =

$$\frac{\text{mol of CH}_3\text{OH converted to each product}}{\text{mol of CH}_3\text{OH fed} - \text{mol of unreacted CH}_3\text{OH}} \times 100$$

Substantial reactivity of methanol (%) =

$$\frac{\text{mol of CH}_3\text{OH fed} - \text{mol of unreacted CH}_3\text{OH} - \text{mol of CH}_3\text{OH converted *1}}{\text{mol of CH}_3\text{OH fed}} \times 100$$

Selectivity to realizable ethanol (%) =

$$\frac{\text{mol of CH}_3\text{OH converted to realizable C}_2\text{H}_5\text{OH*2}}{\text{mole of CH}_3\text{OH fed} - \text{mol of unreacted CH}_3\text{OH} - \text{mol of CH}_3\text{OH converted}} \times 100$$

*1 contains components, such as dimethoxy ethane, methyl esters, etc. from which methanol can easily be recovered through hydrolysis
*2 contains neat ethanol and components, such as acetaldehyde, dimethoxy ethane, methyl ethyl ether, etc., from which ethanol can easily be recovered through hydrogenation or hydrolysis

EXAMPLE 1

Into a Hastelloy shaking type 100 ml autoclave were charged 10 gram (0.128 mol) of benzene, 1.21 g (0.0023 mol) of basic cobalt carbonate [2CoCO$_3$.3Co(OH)$_2$)] and 4.73 g (0.0234 mol) of tri-n-butylphosphine. A mixed gas of H$_2$ and CO (molar ratio of 1:1) was fed into the autoclave until a pressure of 200 kg/cm$^2$G was reached. The mixture was maintained at 230° C. for 1.5 hours. Thereafter the autoclave was cooled and the gas remaining in the autoclave was discharged to the atmosphere. Then 10 g (0.3121 mol) of methanol and 4 g (0.222 mol) of water were charged into the autoclave. CO gas was fed into the autoclave until a pressure of 200 kg/cm$^2$G was reached. The reaction was carried out at 230° C. for 3 hours.

After the reaction, the autoclave was cooled and the gas remaining inside was discharged to the atmosphere. The hydrogen partial pressure was less than 3 kg/cm$^2$G during the reaction. Gas Chromatograph (GC) Analysis (internal standard method) showed the reactivity of methanol to be 33.8% and a selectivity to neat ethanol of 83.5%. Selectivity to each of the following components was as follows:
dimethyl ether: 0.12%
acetaldehyde: 1.41%
methyl formate: 0.61%
ethyl methyl ether: 0.56%
methyl acetate: 1.91%
n-propanol: 2.49%
dimethoxy ethane: 1.41%
ethyl acetate: 0.32%

This shows a substantial reactivity of methanol of 32.9% and selectivity to realizable ethanol of 88.4%.

EXAMPLES 2-4

The procedures of Example 1 were repeated except that the molar ratio of H$_2$O/methanol was 1.0 (Example 2), 0.53 (Example 3) and 0.36 (Example 4). The hydrogen partial pressure in the reaction was less than 0.85 kg/cm$^2$G in Example 3.

The results are shown in Table 1.

EXAMPLES 5-7

The procedures of Example 1 were repeated except that tri-n-propylphosphine (Example 5), tri-n-hexylphosphine (Example 6) or dicobalt octa-carbonyl (Example 7) were used. The results are shown in Table 1.

EXAMPLE 8

The procedure of Example 1 was repeated except that a mixed gas of carbon monoxide (partial pressure of 195 kg/cm$^2$G) and hydrogen (partial pressure of 5 kg/cm$^2$G) was used. The results are shown in Table 1.

TABLE 1

| Example | | 2 | 3 | 4 | 5 | 6 | 7 | 8 |
|---|---|---|---|---|---|---|---|---|
| components | | | | | | | | |
| methanol | g (mol) | 10 (0.3121) | 10 (0.3121) | 10 (0.3121) | 10 (0.3121) | 10 (0.3121) | 10 (0.3121) | 10 (0.3121) |
| water | g (mol) | 5.62 (0.3122) | 3 (0.1667) | 2 (0.1111) | 4 (0.2222) | 4 (0.2222) | 4 (0.2222) | 2 (0.1111) |
| cobalt source | kind | 2CoCO$_3$.3Co(OH)$_2$ | 2CoCO$_3$.3Co(OH)$_2$ | 2CoCO$_3$.3Co(OH)$_2$ | 2CoCO$_3$.3Co(OH)$_2$ | 2CoCO$_3$.3Co(OH)$_2$ | Co$_2$(CO)$_8$ | 2CoCO$_3$.3Co(OH)$_2$ |
| | amount g (mol) | 1.21 (0.0023) | 1.21 (0.0023) | 1.21 (0.0023) | 1.21 (0.0023) | 1.21 (0.0023) | 2 (0.0058) | 1.21 (0.0023) |
| tertiary phosphine | kind | tri-n-butyl phosphine | tri-n-butyl phosphine | tri-n-butyl phosphine | tri-n-propyl phosphine | tri-n-hexyl phosphine | tri-n-butyl phosphine | tri-n-butyl phosphine |
| | amount g (mol) | 4.73 (0.0234) | 4.73 (0.0234) | 4.73 (0.0234) | 3.75 (0.0234) | 6.7 (0.0234) | 4.73 (0.0234) | 4.73 (0.0234) |
| solvent | kind | benzene | benzene | benzene | benzene | benzene | benzene | benzene |
| | amount g (mol) | 10 (0.128) | 10 (0.128) | 10 (0.128) | 10 (0.128) | 10 (0.128) | 10 (0.128) | 10 (0.128) |
| reaction conditions | | | | | | | | |
| CO partial pressure kg/cm$^2$ G | | 200 | 200 | 200 | 200 | 200 | 200 | 195 |
| H$_2$ partial pressure kg/cm$^2$ G | | — | — | — | — | — | — | 5 |
| molar ratio of H$_2$/CO | | — | — | — | — | — | — | 0.026 |
| reaction temperature °C. | | 230 | 230 | 230 | 230 | 230 | 230 | 230 |

TABLE 1-continued

| Example | 2 | 3 | 4 | 5 | 6 | 7 | 8 |
|---|---|---|---|---|---|---|---|
| reaction time hr | 3 | 3 | 3 | 3 | 3 | 3 | 3 |
| reactivity of $CH_3OH$ % | 33.7 | 45.1 | 43.8 | 27.3 | 34.5 | 32.9 | 38.5 |
| substantial reactivity of $CH_3OH$ % | 33.2 | 44.2 | 42.1 | 25.8 | 33.4 | 32.2 | 36.4 |
| selectivity to each components % | | | | | | | |
| ethanol | 81.8 | 76.8 | 70.7 | 78.9 | 81.9 | 81.1 | 67.7 |
| dimethyl ether | 0.12 | 0.09 | 0.09 | 0.15 | 0.24 | 0.12 | 0.51 |
| acetaldehyde | 0.19 | 1.32 | 2.62 | 2.41 | 2.08 | 1.43 | 3.57 |
| methyl formate | 0.06 | 0.20 | 0.31 | 0.57 | 0.51 | 0.38 | 0.82 |
| methyl ethyl ether | 0.37 | 0.67 | 1.03 | 1.26 | 0.83 | 0.57 | 0.94 |
| diethyl ether | — | — | — | — | — | — | — |
| methyl acetate | 1.87 | 2.50 | 4.40 | 4.72 | 3.00 | 2.39 | 5.32 |
| n-propanol | 2.53 | 3.28 | 3.05 | 3.19 | 3.28 | 3.18 | 3.12 |
| dimethoxy ethane | 0.55 | 0.20 | 1.30 | 2.51 | 0.92 | 0.19 | 1.72 |
| ethyl acetate | 0.13 | 0.55 | 1.73 | — | — | — | — |
| realizable ethanol | 83.8 | 80.4 | 78.2 | 87.5 | 87.6 | 84.7 | 77.8 |

COMPARATIVE RUN 1

Into a Hastelloy shaking type 100 ml autoclave were charged 10 gram (0.128 mol) of benzene, 1.21 g (0.0023 mol) of basic cobalt carbonate [$2CoCO_3 \cdot 3Co(OH_2)$] and 4.73 g (0.0234 mol) of tri-n-butylphosphine. A mixed gas of $H_2$ and CO (molar ratio of 1:1) was fed into the vessel until a pressure of 200 kg/cm$^2$G was reached. The mixture was maintained at 230° C. for 1.5 hours. Thereafter the autoclave was cooled and the gas remaining in the autoclave was discharged to the atmosphere. Then 10 g (0.3121 mol) of methanol was charged into the autoclave. CO gas was fed into the autoclave until a pressure of 200 kg/cm$^2$G was reached. The reaction was carried out at 230° C. for 3 hours.

After the reaction, the autoclave was cooled and the gas remaining inside the autoclave was discharged to the atmosphere. Gas Chromatograph (GC) Analysis (internal standard method) showed the reactivity of methanol to be 37.9% and a selectivity to neat ethanol of 26.8%. Selectivity to each of the following components was as follows:
acetaldehyde: 5.86%
methyl formate: 1.45%
ethyl methyl ether: 2.42%
methyl acetate: 27.8%
n-propanol: 0.70%
dimethoxy ethane: 19.2%

This shows a substantial reactivity of methanol of 26.8% and selectivity to realizable ethanol of 57.1%.

When no water was added to the reaction system, byproducts, such as acetaldehyde and methyl acetate, were formed in large amounts, and selectivity to ethanol was low. It was clear from the Examples that when the molar ratio of water to methanol increases, the amount of methyl acetate formed decreases and selectivity to ethanol increases.

COMPARATIVE RUN 2

The procedure of Comparative run 1 was repeated except that a mixed gas of carbon monoxide (partial pressure of 195 kg/cm$^2$G) and hydrogen (partial pressure of 5 kg/cm$^2$G) was used. The results are shown in Table 2.

It is clear from Example 8 and Comparative run 2 that when the molar ratio of hydrogen to carbon monoxide is low and no water is added, selectivity to ethanol is low.

COMPARATIVE RUNS 3-5

The procedure of Comparative run 1 was repeated except that the catalysts as shown in Table 2 were used. The results are shown in Table 2.

It is clear from Comparative runs 3-5 that even when other catalysts are used, selectivity to ethanol is very low and that when iodine is used as a co-catalyst, methyl acetate and acetic acid are mainly formed. Thus, it can be seen that all of the examples were carried out with pretreatment of the catalyst in the absence of methanol or water.

TABLE 2

| Comparative run | | 2 | 3 | 4 | 5 |
|---|---|---|---|---|---|
| components | | | | | |
| methanol | g (mol) | 10 (0.3121) | 10 (0.3121) | 10 (0.3121) | 10 (0.3121) |
| water | g (mol) | — | 4 (0.2222) | 4 (0.2222) | 4 (0.2222) |
| cobalt | kind | $2CoCO_3 \cdot 3Co(OH)_2$ | $CoI_2$ | $CoI_2$ | $2CoCO_3 \cdot 3Co(OH)_2$ |
| source | amount g (mol) | 1.21 (0.0023) | 3.66 (0.0117) | 3.66 (0.0117) | 1.21 (0.0023) |
| tertiary phosphine | kind | tri-n-butyl phosphine | — | tri-n-butyl phosphine | piperidine |
| | amount g (mol) | 4.73 (0.0234) | — | 4.73 (0.0234) | 2 (0.0235) |
| solvent | kind | benzene | benzene | benzene | benzene |
| | amount g (mol) | 10 (0.128) | 10 (0.128) | 10 (0.128) | 10 (0.128) |
| reaction conditions | | | | | |
| CO partial pressure kg/cm$^2$ G | | 195 | 195 | 195 | 195 |
| $H_2$ partial pressure kg/cm$^2$ G | | 5 | — | — | — |
| molar ratio of $H_2$/CO | | 0.026 | — | — | — |
| reaction temperature °C. | | 230 | 230 | 230 | 230 |
| reaction time hr | | 3 | 3 | 3 | 3 |
| reactivity of methanol % | | 39.5 | 92.1 | 96.9 | 18.2 |
| substantial reactivity of methanol % | | 30.6 | 58.1 | 83.2 | 12.1 |

TABLE 2-continued

| Comparative run | 2 | 3 | 4 | 5 |
|---|---|---|---|---|
| selectivity to each components % | | | | |
| ethanol | 32.8 | — | — | — |
| dimethyl ether | t | 16.4 | 3.07 | 0.43 |
| acetaldehyde | 4.85 | 1.08 | 2.46 | — |
| methyl formate | 0.87 | — | 0.22 | 0.81 |
| methyl ethyl ether | 1.89 | 0.11 | — | — |
| methyl acetate | 23.5 | 40.9 | 21.8 | 49.5 |
| acetic acid | — | 12.6 | 31.89 | 3.73 |
| n-propanol | 0.98 | — | — | — |
| dimethoxy ethane | 13.5 | — | — | — |
| ethyl acetate | 2.63 | — | 0.75 | — |
| realizable ethanol | 57.3 | 1.8 | 3.3 | — |

What is claimed is:

1. A process for producing ethanol which comprises reacting methanol, carbon monoxide and water in the presence of a catalyst consisting of cobalt or a cobalt compound and a tertiary phosphine as an effective component, which catalyst has been preliminarily activated by heat-treating at 180°–280° C. and under 50–500 Kg/cm$^2$G in the presence of mixed gas comprising hydrogen and carbon monoxide, wherein the molar ratio of hydrogen to carbon monoxide is more than 0.25, and solvent, and in the substantial absence of methanol and water.

2. The process as defined in claim 1 wherein the amount of the water employed is in the range of 0.05 to 5 mol per 1 mol of methanol.

3. The process as defined in claim 1 wherein tertiary phosphine is used in an amount that the atomic ratio of cobalt to phosphorus is in the range of 1:0.2 to 1:8.

4. The process as defined in claim 1 wherein the cobalt compound is dicobalt octacarbonyl.

5. The process as defined in claim 1 wherein the tertiary phosphine is tri-n-butyl phosphine.

6. The process as defined in claim 1 wherein the reaction is carried out in the presence of a solvent.

7. The process as defined in claim 6 wherein the solvent is benzene.

8. The process as defined in claim 1 wherein the partial pressure of carbon monoxide in the reaction is in the range of 100–500 kg/cm$^2$G.

9. The process as defined in claim 1 wherein the reaction temperature is in the range of 180°–280° C.

* * * * *